United States Patent [19]
Reeves

[11] Patent Number: 5,405,321
[45] Date of Patent: Apr. 11, 1995

[54] COMBINED ASPIRATION AND FLUSHING COUPLING

[75] Inventor: Geoffrey M. Reeves, Queensland, Australia

[73] Assignee: William A. Cook Australia Pty. Ltd., Brisbane, Australia

[21] Appl. No.: 88,879

[22] Filed: Jul. 7, 1993

[30] Foreign Application Priority Data

Jul. 7, 1992 [AU] Australia .................. PL3350

[51] Int. Cl.[6] ............ A61M 3/00; A61M 25/00; A61B 10/00
[52] U.S. Cl. ................... 604/44; 604/283; 128/752; 128/753
[58] Field of Search ............ 604/35, 55, 43–45, 604/280, 27, 283, 28; 128/750, 752, 753, 760, 763, 766

[56] References Cited

U.S. PATENT DOCUMENTS

| | | | |
|---|---|---|---|
| 1,937,362 | 11/1933 | Schellberg | 604/35 X |
| 3,577,992 | 5/1971 | Merry. | |
| 3,606,878 | 9/1971 | Kellogg, Jr. | 128/753 |
| 4,037,599 | 7/1977 | Raulerson | 604/44 |
| 4,299,217 | 11/1981 | Sagae et al. | 604/44 |
| 4,585,435 | 4/1986 | Vaillancourt | 604/27 |
| 4,692,140 | 9/1987 | Olson | 604/40 |
| 4,791,937 | 12/1988 | Wang | 128/752 |
| 4,824,434 | 4/1989 | Seitz, Jr. | 604/27 |
| 4,982,739 | 1/1991 | Hemstreet et al. | 128/750 |
| 4,994,048 | 2/1991 | Metzger | 604/283 |
| 5,024,654 | 6/1991 | Tyler | 604/43 |
| 5,160,319 | 11/1992 | Emery et al. | 604/27 |

FOREIGN PATENT DOCUMENTS

| | | |
|---|---|---|
| 0337617 | 10/1989 | European Pat. Off. . |
| 3522782 | 1/1987 | Germany . |
| 8606968 | 12/1986 | WIPO .................. 604/44 |

Primary Examiner—John D. Yasko
Assistant Examiner—Adam J. Cermak
Attorney, Agent, or Firm—Richard J. Godlewski

[57] ABSTRACT

A medical coupling device (8) as part of a medical system for withdrawing an ovum from a follicle. The coupling device has an inner chamber (3) that is formed from first (1) and second (2) parts, which are press-fitted together or slidably fitted together by means of male and female engagement parts (6). The inner chamber has a pair of axial openings (4) for receiving a first conduit (9) and a lateral opening (5) for receiving a second conduit (10) therein. In one embodiment, the first conduit includes a single lumen and a side port (11) of which the second conduit is in fluid communication with the single lumen of the first conduit in the inner chamber of the coupling device. In a second embodiment, the first conduit includes multiple lumens (12,13), of which only one of the lumens of the first conduit has a side port that is in fluid communication with the second conduit in the inner chamber of the coupling device. An outer covering (16), preferably of a plastic material, is formed over the first and second parts along with the first and second conduits to provide a seal for the device and the conduits. The plastic outer covering also provides a color code for designating a characteristic of the device, such as the gauge of the conduits.

13 Claims, 2 Drawing Sheets

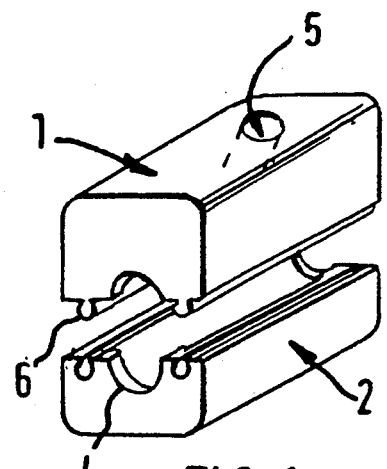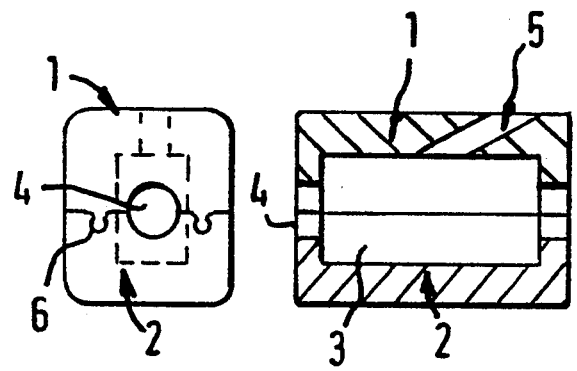
FIG.1a  FIG.1b  FIG.1c
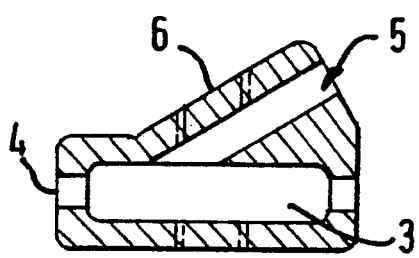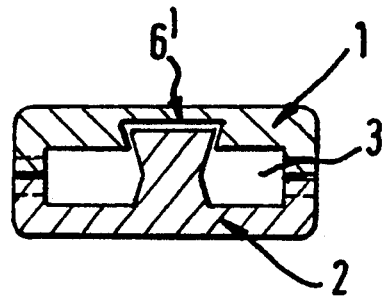
FIG.1d  FIG.1e
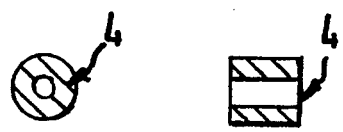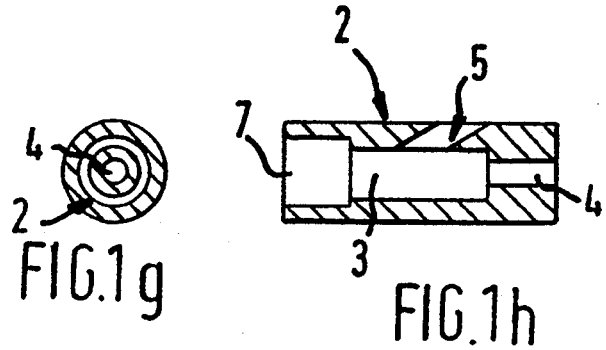
FIG.1f  FIG.1g  FIG.1h

COMBINED ASPIRATION AND FLUSHING COUPLING

TECHNICAL FIELD

This invention relates in general to coupling devices for use in medical systems.

BACKGROUND OF THE INVENTION

One step of the in vitro fertilization (I.V.F.) program is the removal of an ovum (egg) from the follicle (egg sac) of a woman patient. This is usually achieved by piercing the follicle with one end of a long hollow tapered conduit or needle and applying a vacuum to the other end of the needle so as to withdraw the ovum from the follicle together with the fluid contained in the follicle and transfer the ovum and fluid to a receptacle, such as a test tube. For a variety of reasons, the ovum is sometimes not completely transferred. When this occurs, it is necessary to introduce fluid into the follicle in an attempt to flush out the ovum and thus attempt the withdrawal again.

In order to reduce the risk of injury to the patient, the follicle and the ovum, it is preferable to have a method that allows both the delivery of fluid and aspiration of fluid through a single needle or conduit. One way of achieving this is to have a control device attached to the needle or conduit, said device having two inlets, one to deliver the flushing fluid and one to aspirate fluid from the follicle.

A number of such control devices are currently available, but they do have certain disadvantages. For example, they may incorporate plastic valves with compressible fittings that may leak after heat sterilization. Alternatively, they may be constructed entirely from metal which means that they are difficult and expensive to manufacture. Additionally, such control devices may be bulky and difficult for the surgeon to handle during the I.V.F. procedure.

SUMMARY OF THE INVENTION

According to the present invention there is provided a medical coupling device to form part of a medical system designed to withdraw an ovum from a follicle, said system comprising a first conduit means, extending from the follicle, via the coupling device to an aspiration arrangement at which the ovum is to be collected, said system also comprising a second conduit means extending from a source of flushing media to the coupling device in which connection between the first and second conduit means occurs, whereby flushing media can be applied to the follicle to assist in the withdrawal of the ovum, the coupling device comprises an inner chamber and first means for terminating the said second conduit means in the chamber, in that the first conduit means has a lumen therein adapted to be in fluid communication with the said inner chamber, and in that the device also comprises means for sealing the first and second conduit means with respect to the said chamber.

In an embodiment of the invention there is provided a combined plastic aspiration and flushing control device comprising a small plastic "inner" fitting that attaches securely to a first conduit means, such as a needle, which may be inserted into a follicle. This fitting additionally allows the attachment of a second conduit means, such that the lumen of the second conduit means is in fluid communication with the lumen of the first conduit means. In the event that the latter contains several lumens, the other lumen or lumens do not communicate with the lumen of the second conduit means. A plastic "outer" covering that seals and secures the said inner fitting and the first and second conduit means, results in a coupling device which is compact, ergonomic, and/or leak-resistant.

In one particular embodiment, the inner fitting and/or outer covering are color-coded to indicate a particular characteristic of the combined valve and/or device, such as the gauge of the first conduit means.

The embodiment of the invention provides an improved combined aspiration and flushing device that is compact, ergonomic, efficient, cheaper to manufacture and resistant to leaking. It may also be color-coded to indicate a particular characteristic of the invention, such as the gauge of the first conduit means.

BRIEF DESCRIPTION OF THE DRAWING

FIGS. 1a, 1b and 1c show a perspective view, an end view, and a cross-sectional side cut-away view of an embodiment of the coupling device, FIG. 1b being of a relatively small device;

FIGS. 1d and 1e show a cross-sectional side cut-away view of another embodiment of the coupling device, and a cross-sectional top cut-away view;

FIG. 1f shows cross-sectional end and side views of a plug, FIGS. 1g and 1h are cross-sectional end and side views of another embodiment of the device with the plug inserted in the device;

DETAILED DESCRIPTION

Figure 2:
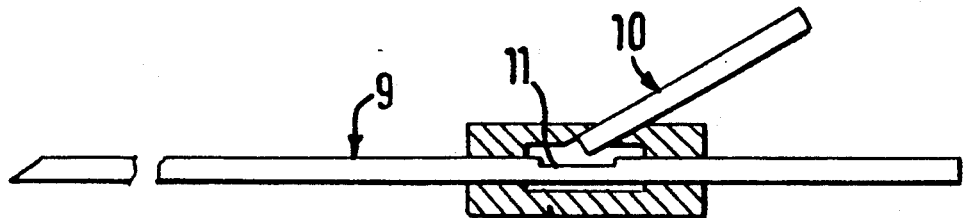
FIGS. 2 and 3 show schematic diagrams, partly in cross-section, of two embodiments of the device to which first and second conduits have been attached.

FIGS. 1a, 1b and 1c illustrate one form of coupling device comprising first (1) and second (2) parts which can be press-fitted together, or slidably fitted together, by means of male and female engagement parts (6). The device comprises an inner chamber 3 with a pair of axial openings 4 for receiving a first conduit 9 (FIG. 2), and an opening 5 for receiving a second conduit 10 (FIG. 2). Parts 1 and 2 are preferably made of plastic material, the latter being selected to be capable of being sterilized and being sufficiently rigid so that it can support the conduits.

FIGS. 1d and 1e illustrate another form of coupling device, also formed of two parts 1 and 2 and forming an inner chamber 3 when fitted together. The press fitting in this embodiment is formed by a wedge chipping or press fitting into an associated socket 6'. The first conduit 9 again fits through axial openings 4 and the second conduit 10 fits through opening 5, in a similar manner to the FIG. 1a embodiment.

FIGS. 1f, 1g and 1h illustrate a further form of coupling device, again being formed of two parts 1 and 2, but with the axial aperture 4 at the left hand end of FIG. 1h, being an aperture in a plug which fits into the cavity 7 of the device. Again, the first conduit 9 extends between the apertures 4 and the second conduit 10 enters the aperture 5.

In the embodiment shown in FIG. 2, the first conduit 9 is a single lumen conduit and is assembled in the coupling device 8, with the left hand end of the conduit or needle or cannula sharpened to facilitate penetration of the follicle. The right hand end of first conduit extends to an aspiration arrangement by which vacuum is applied to the lumen to facilitate removal of the ovum from the follicle. The second conduit 10 enters the opening 5 and the lumen of conduit 10 is thus in fluid communication with the inner chamber 3 of the device. A section of the wall of the first conduit 9 is removed to provide a port 11 by which the lumen of conduit 9 is also in fluid communication with the inner chamber 3.

The second lumen is provided in order to supply a flushing fluid to the follicle to facilitate removal of the ovum therefrom, in the event that normal aspiration proves to be insufficient for ovum removal. Whilst flushing fluid is applied to the follicle, a valve (not shown) is provided so that the fluid is correctly applied to the follicle and not to the aspiration arrangement. The valve can be attached, by for example a screw fitting, to the right hand end of the device 8, and controls flow of fluid in the lumen at the right hand end of the first conduit. The valve can be located either at the coupling device, or at the aspiration arrangement, or at any location therebetween. It can also be provided within or on the outer plastic covering 16, as herein described. As a consequence, the lumen of the second conduit means is in continuous fluid communication with the fluid in the inner chamber 3 and fluid in the lumen of the first conduit.

Figure 3:
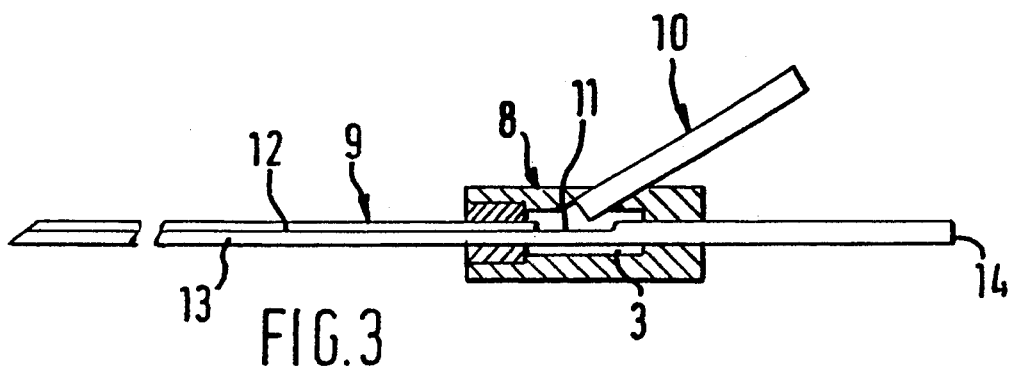

In the embodiment shown in FIG. 3, a device similar to that shown in FIG. 1h is provided. A multi-lumen, such as dual lumen, catheter with lumens 12 and 13 is positioned within the openings 4. A section 11 of the wall of the dual lumen is removed to provide fluid communication between one lumen only namely lumen 12 of the conduit 1 and the inner chamber 3. Flushing fluid from conduit 10 will have a similar effect to that of FIG. 2 except that the said one lumen of this conduit can be blocked off to prevent flushing fluid from passing to the aspiration arrangement. If it is required for the said one lumen to be left open, then a valve, similar to that described in connection with FIG. 2 can be provided to block off the said one lumen. The other of the dual lumens can, but need not be, controlled by a valve, and can thus be left open to receive at the opening 14 the ovum along with the flushing fluid.

As a consequence, the lumen of the second conduit is in continuous fluid communication with only lumen 12 of the first conduit.

The first conduit in all embodiments is shown as extending between the pointed needle end thereof and the end 14 at the aspiration arrangement. Clearly, the first conduit in the FIG. 2 embodiment can be in two parts, each in communication with the chamber 3. Similar consideration can apply to the FIG. 3 embodiment, or the dual lumen conduit can be made as two separate single lumen conduits with only one of them in communication with the inner chamber 3.

Figure 4:
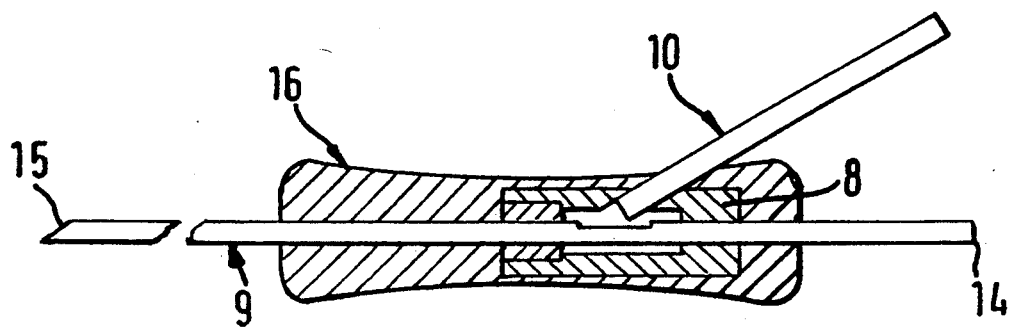
FIGS. 4 and 5 show schematic diagrams, again partly in cross-section of embodiments of the device to which an outer covering and seal has been applied.

The embodiment shown in FIG. 4 is the coupling device of FIG. 3 to which an outer covering 16 preferably of plastic material has been applied. The plastic is molded over the device 8 and over the first and second conduits in such a way that it provides a seal for the device 8 and the conduits 9 and 10, and also firmly secures the conduits in position. This provides an ergonomic way for gripping the device and can also provide a method for color coding to identify a particular characteristic of the invention, such as the gauge of the first conduit. The device of FIG. 4 differs from the device of FIG. 3 in that a single lumen first conduit is employed. An opening can be provided at the right hand end of the covering 16 in order to receive a control valve such as a Luer lock. A screw thread can be provided on the internal surface of such an opening so that the Luer lock can be screwed in position. The lock will have an axial aperture therethrough and it will control the flow of fluid through the conduit in that axial aperture.

Figure 5:
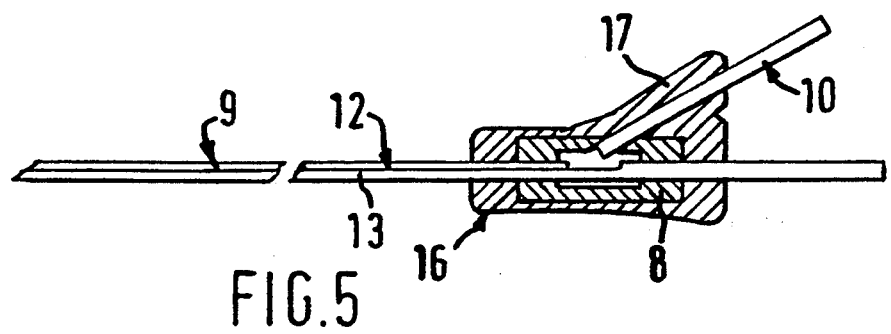

The embodiment shown in FIG. 5 is the coupling device of FIG. 2 in which an outer covering 16 has been applied. Again the covering 16 is preferably of plastic material, and again is of a material capable of being sterilized. The first conduit in this embodiment has two lumens 12 and 13 and the same considerations as in FIG. 3 apply. Additional covering material 17 is applied over the second conduit at the entry to the device to provide additional strength and sealing. The outer covering 16 and 17 in the embodiments of FIGS. 4 and 5 may extend significantly along either or both of the conduits, in order to provide further additional strength and sealing. The embodiment of FIG. 5 may also be provided with a valve such as a Luer lock as described in connection with the FIG. 4 embodiment.

A third conduit means can be inserted down a lumen of the first conduit. That requires the incorporation of a connection means on the device 8 to enable the third conduit to be easily inserted and attached in a leak proof manner, such as by a Luer lock or other connection means. This will permit the attachment of other conduits, fittings, or stylets to the device.

Each of the above devices is for use in conjunction with a medical system comprising means for the aspiration of fluid and means for the flushing of fluid. In one particular embodiment shown in FIG. 4, the sharpened end 15 of the arrangement is applied to the other end 14 of the first conduit means 9 is introduced into a follicle. Vacuum or the aspiration arrangement is applied to the other end 14 of the first conduit means 9 in order to aspirate an ovum and fluid from the follicle. At that time, the second conduit means 10 is sealed off and does not provide fluid to chamber 3. Subsequently, end 14 is sealed off, and replacement fluid is reintroduced into the follicle via the first conduit means by a flushing means attached to the second conduit means 10. That is, replacement fluid is passed down the lumen of the second conduit means 10, into the chamber 3, through the port 11, and through the lumen of the first conduit means 9 into the follicle. The process of aspiration is then re-initiated.

In the embodiment of the invention, shown in FIG. 3 or 5, the first conduit means has, in part, two lumens 12 and 13. The ovum and fluid is aspirated through one lumen 13 of the first conduit means 9 and replacement fluid is subsequently or simultaneously reintroduced into the follicle through the other lumen 12 of the first conduit means 9, via a flushing device attached to the second conduit means 10. That is, replacement fluid is reintroduced down the lumen of the second conduit means, into the chamber 3, through the port 11 and along lumen 12 of the first conduit means into the follicle.

What is claimed is:

1. A medical system for withdrawing an ovum from a follicle, comprising a coupling device (8), a first conduit (9) for extending from the follicle via the coupling device (8) to an aspiration arrangement for collecting the ovum thereat, a second conduit (10) for extending from a source of flushing media to the coupling device in which the first and the second conduits are in fluid communication, whereby flushing media is applied to the follicle to assist in the withdrawal of the ovum, wherein the coupling device comprises an inner chamber (3) and first and second parts (1,2) that fit together to form the inner chamber, the first and second parts having openings (4,5) therein for introduction of the first and the second conduits through the openings, wherein the first conduit has a lumen therein for fluid communication with the inner chamber, and wherein the coupling device also comprises a plastic material (16, 17) extending over the outer surface of the coupling device and at least one of the first and the second conduits.

2. The medical system according to claim 1 wherein the first conduit is a single lumen conduit for extension from an outlet of the inner chamber to the aspiration arrangement.

3. The medical system according to claim 1 wherein the first and the second parts and the plastic material include a color code.

4. The medical system according to claim 1 wherein the first conduit has a first and a second lumen and wherein the second lumen is for extension from the follicle to the aspiration arrangement without fluid communication with the inner chamber.

5. The medical system according to claim 4 wherein the first and the second parts and the plastic material include a color code.

6. The medical system according to claim 1 wherein the first and the second parts are assembled together by means of at least one of a push fitting and a sliding fitting incorporated therein.

7. The medical system according to claim 1 wherein the first and the second parts and the plastic material include a color code.

8. A medical system for withdrawing an ovum from a follicle, comprising a coupling device, a first conduit having a single lumen therein and for extending from the follicle via the coupling device to an aspiration arrangement for collection of the ovum thereat and a second conduit for extending from a source of flushing media to the coupling device for connection of the first and the second conduits, whereby flushing media is applied to the follicle to assist in the withdrawal of the ovum; said coupling device comprising:

an inner chamber, the lumen of the first conduit for fluid communication with the inner chamber;

first and second parts that fit together to form the inner chamber, with openings therein for introduction of the first and the second conduits; and means for sealing the first and the second conduits with respect to the chamber formed by the first and the second parts when fitted together.

9. The medical system according to claim 8 wherein at least one of the first conduit and the second conduit is positioned in the chamber.

10. The medical system of the previous claim 9 wherein the first and the second parts are assembled together by at least one of a push fitting and a sliding fitting incorporated therein.

11. The medical system of claim 10 wherein the first and the second parts and the plastic material include a color code.

12. The medical system of claim 8 wherein the first conduit has a first and a second lumen and wherein the second lumen is for extension from the follicle to the aspiration arrangement without fluid communication with the inner chamber.

13. A medical system for withdrawing an ovum from a follicle, comprising a coupling device, a first conduit having a first and a second lumen therein and for extending from the follicle via the coupling device to an aspiration arrangement for collection of the ovum thereat and a second conduit for extending from a source of flushing media to the coupling device for connection of the first and second conduits whereby flushing media is applied to the follicle to assist in withdrawal of the ovum; said coupling device comprising:

first and second parts that are assembled together by at least one of a push fitting and a sliding fitting incorporated therein and that form together an inner chamber, with openings therein for introduction of the first and second conduits prior to the fitting of the first and the second parts, the first lumen of the first conduit for fluid communication with the inner chamber, the second lumen for extension from the follicle to the aspiration arrangement without fluid communication with the inner chamber;

first means for terminating the second conduit in the inner chamber; and a plastic material extending over an outer surface of the coupling device and at least one of the first and the second conduits for sealing the first and the second conduits with respect to the chamber, the first and the second parts and the plastic material having a color code to indicate a particular characteristic of the device.

* * * * *